United States Patent [19]

Patil

[11] 4,309,777
[45] Jan. 12, 1982

[54] ARTIFICIAL INTERVERTEBRAL DISC

[76] Inventor: Arun A. Patil, 1011 Valley View Dr., Minot, N. Dak. 58701

[21] Appl. No.: 206,564

[22] Filed: Nov. 13, 1980

[51] Int. Cl.³ .............................................. A61F 1/24
[52] U.S. Cl. ..................................... 3/1.91; 128/92 C
[58] Field of Search ........................... 3/1.91, 1.9, 1; 128/92 C, 92 R, 92 G, 334 R

[56] References Cited

U.S. PATENT DOCUMENTS

| | | | |
|---|---|---|---|
| 2,677,369 | 5/1954 | Knowles | 128/92 R |
| 3,426,364 | 2/1969 | Lumb | 3/1.91 |
| 3,867,728 | 2/1975 | Stubstad et al. | 3/1.91 |
| 3,987,499 | 10/1976 | Scharbach et al. | 3/1.91 |

FOREIGN PATENT DOCUMENTS

| | | | |
|---|---|---|---|
| 2263842 | 7/1974 | Fed. Rep. of Germany | 3/1.91 |
| 1122634 | 5/1956 | France | 128/92 C |

*Primary Examiner*—Ronald L. Frinks
*Attorney, Agent, or Firm*—Zarley, McKee, Thomte, Voorhees & Sease

[57] ABSTRACT

An artificial intervertebral disc for implantation in the disc space after the removal of a diseased or damaged cervical intervertebral is described and comprises upper and lower disc portions having a plurality of springs positioned therebetween to yieldably urge the disc portions away from each other. A plurality of spikes extend upwardly from the upper disc portion for engagement with the vertebra thereabove. A plurality of spikes extend downwardly from the lower end of the lower disc portion for engagement with the vertebra therebelow.

6 Claims, 4 Drawing Figures

ARTIFICIAL INTERVERTEBRAL DISC

BACKGROUND OF THE INVENTION

This invention relates to an artificial intervertebral disc and more particularly to a stainless steel disc which is implanted in the disc space after a diseased or damaged cervical intervertebral disc has been removed.

Many types of artificial intervertebral discs have been previously described. For example, U.S. Pat. No. 3,867,728 discloses a prosthesis for spinal repair but the prosthesis is constructed of a resilient material such as an elastic polymer. Further examples are illustrated in U.S. Pat. Nos. 2,677,369 and 3,426,364. Although the devices of the prior art may have met with some success, it is believed that the instant invention represents a significant advance in the art due to the fact that the size of the same may be varied and due to the fact that the springs contained therein may be varied to achieve the desired vertebrae separation.

Therefore, it is a principal object of the invention to provide an improved artificial intervertebral disc.

A further object of the invention is to provide an artificial intervertebral disc which includes a plurality of springs positioned between upper and lower disc portions.

A still further object of the invention is to provide an artificial intervertebral disc including means for achieving a positive implantation in the disc space after the removal of a diseased or damaged cervical intervertebral disc.

A still further object of the invention is to provide an artificial intervertebral disc which is economical of manufacture.

These and other objects will be apparent to those skilled in the art.

SUMMARY OF THE INVENTION

An artificial intervertebral disc is described which is implanted in the disc space after the removal of a diseased or damaged cervical intervertebral disc. The disc is comprised of upper and lower disc portions having spikes extending upwardly and downwardly from the upper and lower surfaces thereof for engagement with the vertebrae adjacent thereto. A plurality of compression springs are positioned between the disc portions to yieldably urge the disc portions away from each other.

DESCRIPTION OF THE PREFERRED EMBODIMENT

Figure 1:
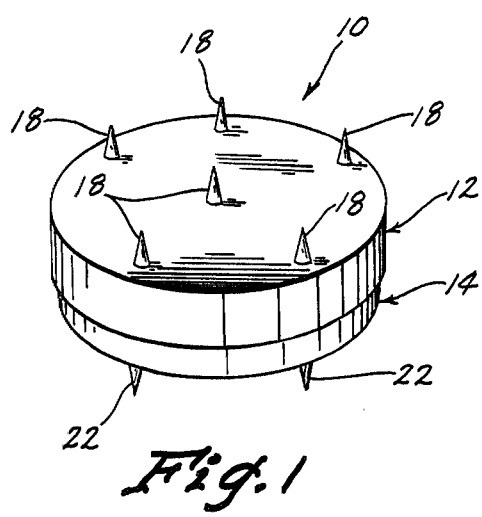
FIG. 1 is a perspective view of the artificial intervertebral disc of this invention.
Figure 2:
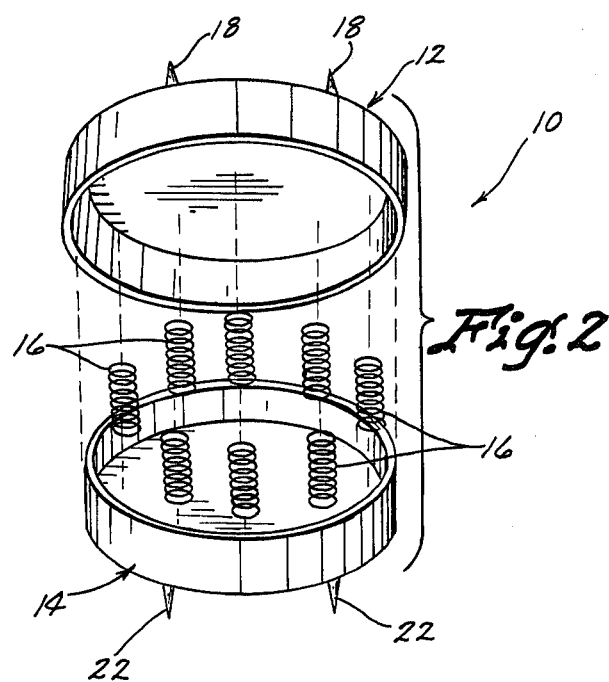
FIG. 2 is an exploded perspective view of the disc of this invention.
Figure 3:
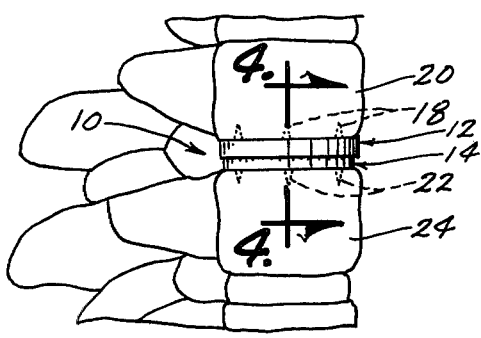
FIG. 3 is a side elevational view illustrating the disc of this invention implanted in the disc space after the removal of a diseased or damaged cervical intervertebral disc.
Figure 4:
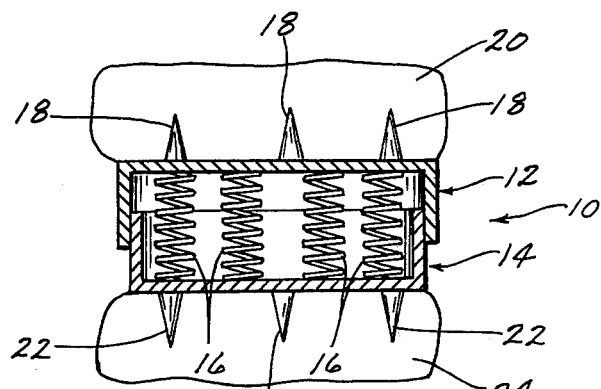
FIG. 4 is an enlarged sectional view seen on lines 4—4 of FIG. 3.

The artificial intervertebral disc of this invention is referred to generally by the reference numeral 10 and generally comprises upper and lower disc portions 12 and 14 respectively. Disc portions 12 and 14 are generally cup-shaped with one of the disc portions having a slightly larger diameter than the other so that one of the disc portions may be partially embraced by the other as illustrated in FIGS. 1 and 4. Preferably, the disc portions 12 and 14 are comprised of a stainless steel or other metal material. A plurality of compression springs 16 are positioned between the disc portions 12 and 14 as best seen in FIGS. 2 and 4 to yieldably urge the disc portions 12 and 14 away from each other.

Disc portion 12 is provided with a plurality of spikes 18 which extend upwardly therefrom for engagement with the vertebra 20 as will be described in more detail hereinafter. Likewise, a plurality of spikes 22 extend downwardly from the lower end or surface of disc portion 14 for engagement with the vertebra 24 as will also be described in more detail hereinafter. In the preferred embodiment, it is recommended that the springs 16 have a strength capable of withstanding twelve pounds force so that the upper and lower surfaces of the disc 12 are maintained approximately six millimeters apart. In the preferred embodiment, the diameter of the disc is recommended to be one centimeter with the maximum height of the disc being approximately six millimeters. It is also recommended that the minimum height of the disc be four millimeters with the height of the spikes being approximately one millimeter.

The disc 10 is implanted after an interior diskectomy is performed. The disc space is further widened by applying skeletal traction on the spine. During implantation, the upper and lower lid portions 12 and 14 are maintained closely together by securing one or two wires therearound. After implantation, the wires will be cut and pulled from the space thereby allowing the lid portions 12 and 14 to move in opposite directions to exert an outward pressure and to cause the spikes 18 and 22 to engage the vertebrae 20 and 24. The number and strength of the springs may be varied as required depending on the particular medical complications being faced. The springs assert outward pressure thereby causing distraction to open the neural foramen. Thus it can be seen that a novel artificial intervertebral disc has been described which accomplishes at least all of its stated objectives.

I claim:

1. An artificial intervertebral disc for implantations in the disc space after the removal of a diseased or damaged cervical intervertebral disc, comprising, an upper disc portion, a lower disc portion mounted on said upper disc portion, said upper disc portion having spike means extending upwardly from the upper end thereof for engagement with the vertebra thereabove, said lower disc portion having spike means extending downwardly from the lower end thereof for engagement with the vertebra therebelow, and spring means positioned between said upper and lower disc portion yieldably urging said disc portions away from each other.

2. The disc of claim 1 wherein said disc portions are cup-shaped.

3. The disc of claim 1 wherein said spring means comprises a a plurality of compression springs positioned between and engaging said disc portions.

4. The disc of claim 1 wherein said one of said disc portions partially embraces the other of said disc portions.

5. The disc of claim 1 wherein said disc portions are comprised of stainless steel.

6. The disc of claim 1 wherein said spike means comprises a plurality of spaced apart spike members.

* * * * *